United States Patent [19]

Blaylock

[11] Patent Number: 4,842,783
[45] Date of Patent: Jun. 27, 1989

[54] METHOD OF PRODUCING FIBER OPTIC CHEMICAL SENSORS INCORPORATING PHOTOCROSSLINKED POLYMER GELS

[75] Inventor: Mark E. Blaylock, Miami, Fla.

[73] Assignee: Cordis Corporation, Miami, Fla.

[21] Appl. No.: 92,645

[22] Filed: Sep. 3, 1987

[51] Int. Cl.$^4$ .................... G02B 6/02; B29D 11/00
[52] U.S. Cl. .................................. 264/1.4; 8/509;
8/514; 128/634; 264/1.5; 264/78; 350/96.3
[58] Field of Search ............... 264/1.1, 1.4, 1.5, 1.7,
264/22, 46.6, 78, 272.16; 128/634, 636, 667;
350/96.29, 96.3; 8/493, 507, 509, 514

[56] References Cited

U.S. PATENT DOCUMENTS

| Re. 32,475 | 8/1987 | Nishida et al. | |
|---|---|---|---|
| 4,200,110 | 4/1980 | Peterson et al. | |
| 4,476,870 | 10/1984 | Peterson et al. | 128/666 |
| 4,577,109 | 3/1986 | Hirschfeld | |
| 4,682,895 | 7/1987 | Costello | 128/636 |

FOREIGN PATENT DOCUMENTS

| 73558 | 9/1983 | European Pat. Off. | 128/634 |
|---|---|---|---|
| 228939 | 10/1986 | Japan | 264/1.7 |
| 83/03344 | 10/1983 | PCT Int'l Appl. | 128/634 |

*Primary Examiner*—James Lowe
*Attorney, Agent, or Firm*—Lockwood, Alex, Fitzgibbon & Cummings

[57] ABSTRACT

A fiber optic chemical sensor and the method of making it are provided, such being useful in medical, biological and industrial applications. The sensor includes an optical fiber waveguide having a photocrosslinked polymeric gel at a portion thereof, which gel is crosslinked in place and undergoes substantial volume expansion. A dye is absorbed into the gel, the dye being responsive to different degrees depending on the presence and concentration of any one of particular parameters of a fluid being monitored, such parameters being pH, oxygen concentration, carbon dioxide concentration and the like.

10 Claims, 1 Drawing Sheet

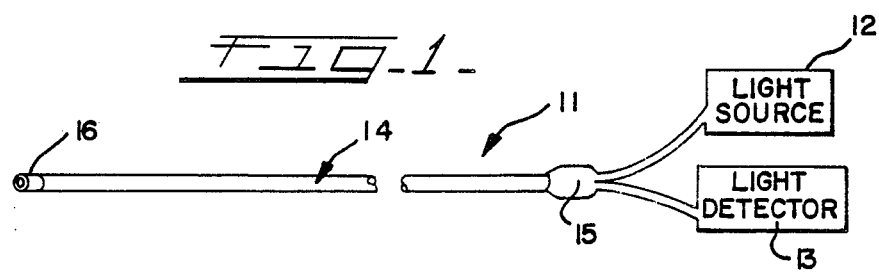
FIG-1-
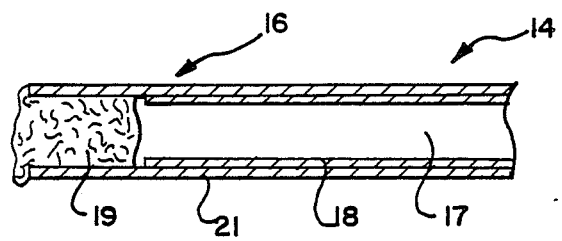
FIG-2-
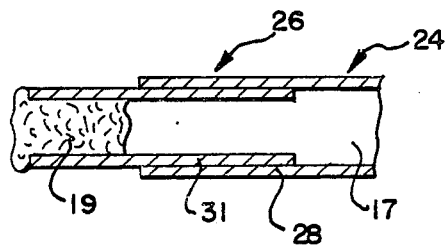
FIG-3-
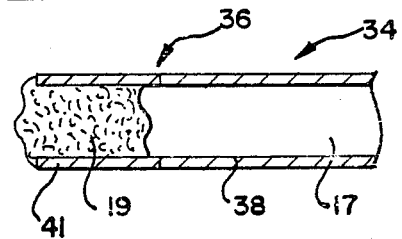
FIG-4-

METHOD OF PRODUCING FIBER OPTIC CHEMICAL SENSORS INCORPORATING PHOTOCROSSLINKED POLYMER GELS

BACKGROUND AND DESCRIPTION OF THE INVENTION

The present invention generally relates to chemical sensors for monitoring, detecting and/or measuring parameters at locations remote from detection instrumentation. More particularly, the invention relates to chemical sensor components that are positioned at a remote or distal portion of an optical fiber waveguide, which chemical sensor components incorporate a polymer gel that was photocrosslinked in place and into which a dye component has been absorbed, the dye component being responsive to a parameter within a fluid being monitored.

Fiber optical chemical sensors are generally known to be useful for a wide variety of purposes, especially in the areas of medicine, scientific research, industrial applications, and the like. Descriptive materials that discuss the structure, properties, functions and operational details of fiber optic chemical sensors include U.S. Pat. No. 4,577,109 (Hirschfeld) and Sietz, "Chemical Sensors Based on Fiber Optics", *Analytical Chemistry*, Vol. 56, No. 1, January, 1984, each of which is incorporated by reference hereinto. From publications such as these, it is known to incorporate a chemical sensor into a fiber optic waveguide in a manner such that the chemical sensor will interact with the analyte. The chemical sensor composition and analyte interaction results in a change in optical properties, which change is probed and detected through the fiber optic waveguide. These optical properties of the chemical sensor compositions typically involve changes in colors or in color intensities. In these types of systems, it is possible to detect particularly minute changes in the parameter being monitored in order to thereby provide especially sensitive monitoring capabilities.

A specific application of this fiber optic chemical sensor technology is found in U.S. Pat. No. 4,200,110 (Peterson et al), which shows a fiber optic pH probe. This patent is incorporated by reference hereinto. Other parameters that are typically suitable for measurement by fiber optic chemical sensors include oxygen concentrations and carbon dioxide concentrations which, together with pH, are typical blood parameters that need to be monitored in vivo. Fiber optic chemical sensors can also be used to detect metal ions such as $Al^{+++}$ and $Be^{++}$ and other metal ions that can be determined fluorometrically when in solution, including $Mg^{++}$, $Zn^{++}$ and $Cd^{++}$. Other uses for these types of devices include detection of biological fluids, glucose, ammonia, $UO^{++}$ and halides, the detection of which may require that reagents be diffused into the sample. Other areas in which fiber optic chemical sensors may be useful include the monitoring of chemical conditions during industrial processes, such as for taking industrial biological measurements. An example of a specific industrial type of application could include the use of long-length optical fibers in order to measure conditions within submerged wells or the like.

A typical approach in the construction of fiber optic chemical sensors requires the positioning of the dye material at a generally distal location with the assistance of various different support means. The support means must be such as to permit interaction between the dye material and the substance being subjected to monitoring, measurement and/or detection. Exemplary means include permeable membranes, microencapsulation, and the use of a gel-like support. Formation of a gel-like support can include a procedure of polymerizing monomers which can be volatile and potentially toxic in the presence of a crosslinking agent. Such a procedure tends to require relatively long production time periods and appropriate monomer polymerization conditions.

It has been found that, by proceeding in accordance with the present invention, it is possible to rapidly and efficiently provide a fiber optic chemical sensor having a polymeric gel that suitably positions the dye material. Polymers are used which are of a type that can be crosslinked while within or on the distal end portion of the fiber optic waveguide, which crosslinking takes place rapidly and can be controlled to a substantial degree.

In summary, the present invention is a fiber optic chemical sensor and method for making same, which product and method utilize photocrosslinkable polymers that rapidly crosslink when subjected to actinic radiation. Such photocrosslinking is accomplished in place while the polymer is positioned at the distal end portion of a fiber optic waveguide. The dye material is thereafter absorbed into the photocrosslinked polymer in order to form a dye-containing crosslinked polymeric gel. In their pre-crosslinked condition, the gel-producing crosslinkable polymers suitable for use in accordance with this invention are soluble in a suitable solvent and typically include a vinyl-type base polymer component, especially of the vinyl aromatic type, which base polymer is preferably modified by covalent attachment of vinyl and/or acrylic groups, and same may be further modified by covalent attachment of additional chemical groups.

It is a general object of the present invention to provide an improved fiber optic chemical sensor.

Another object of the present invention is to provide an improved fiber optic chemical sensor that utilizes photoinitiated crosslinking of a polymer in order to form an expanded-volume polymer gel.

Another object of the present invention is to provide an improved fiber optic chemical sensor by a method which photocrosslinks a polymer in place within an optical fiber.

Another object of this invention is to provide an improved fiber optic chemical sensor which incorporates a dye material that fluoresces or otherwise modifies its color or color intensity in response to an analyte.

Another object of the present invention is to provide an improved fiber optic chemical sensor without requiring pretreatment of the fiber optic to adhere the polymeric support material to the fiber optic.

These and other objects, features and advantages of this invention will be clearly understood through a consideration of the following detailed description.

BRIEF DESCRIPTION OF THE DRAWINGS

In the course of this description, reference will be made to the attached drawings, wherein:

FIG. 1 is a generally schematic, perspective view, partially broken away, of a fiber optic chemical sensor device;

FIG. 2 is an enlarged, sectional view of the distal end portion of a preferred embodiment of the fiber optic chemical sensor according to the present invention;

FIG. 3 is a sectional view of another embodiment of the distal end portion of the fiber optic chemical sensor; and FIG. 4 is a sectional view of a further embodiment of the distal end portion of the fiber optic chemical sensor.

DESCRIPTION OF THE PARTICULAR EMBODIMENTS

A fiber optic chemical sensor device is generally designated as 11 in FIG. 1. Device 11 includes a light source 12 for directing probe radiation into the device, as well as a light detector 13 for sensing and detecting radiation from the device. Device 11 includes one or more optical fibers 14 that are joined to light source 12 and to light detector 13 through a suitable junction assembly 15 at a location that is proximal of the distal end portion 16 of the optical fiber 14.

Each optical fiber 14 includes a core 17 surrounded by a cladding or covering 18. Distal end portion 16 includes a photocrosslinked polymeric gel membrane or plug 19. Typically, it is desirable to have the photocrosslinked polymeric gel membrane or plug 19 position such that the substantial extent of its surface can be exposed to actinic radiation that is received at the distal end portion 16 of the optical fiber 14. In the embodiment illustrated in FIG. 2, a capillary tube 21 overlies the cladding 18 at the distal end portion 16. Preferably, such capillary tube may be made of a porous material such as a porous glass or the like. Such capillary tube in the embodiment illustrated in FIG. 2 is concentric with and positioned over the cladding or covering 18. Other suitable arrangements can be utilized, such as those illustrated in FIG. 3 and in FIG. 4.

In FIG. 3, a capillary tube 31 is concentric with and positioned within cladding or covering 28 defining the core 17 of the optical fiber 24. The capillary tube 31 is positioned at the distal end 26 of the optical fiber 24. In FIG. 4, the photocrosslinked polymeric gel membrane or plug 19 had been formed within a capillary tube 41 that is concentric with and substantially the same size as the cladding or covering 38 of the optical fiber 34. The capillary tube 41 is affixed to the cladding or covering 38 in order to form the distal end portion 36 of this embodiment.

The photocrosslinkable polymeric material is positioned within the distal end portion and subjected to actinic radiation so as to be photocrosslinked in place and form the polymeric gel membrane or plug 19 within the distal end portion. A dye component is absorbed into the photocrosslinked polymeric gel in order to form the completed membrane or plug 19. When in used, the dye component of the membrane or plug 19 will change in response to various wavelengths, and such changes are indicative of the parameter being measured. Typically upon application of the light source 12, such changes in the dye are monitored by the light detector 13 for purposes of quantifying the thus measured parameter.

Optical fiber 14 may be of any suitable type that is of a small diameter and that is capable of passing actinic radiation or light therethrough. The diameter of such an optical fiber, for example, can be between approximately 50 and 500 microns. Its core 17 functions to transmit light or actinic radiation, and its covering or cladding 18 functions to refract same. Materials out of which such optical fibers are made are well-known. Generally speaking, the optical fiber need not be confined to one having a discrete core and cladding configuration, but same may be in the nature of a stepped index fiber or a graded index fiber.

The polymeric material of the photocrosslinked polymeric gel membrane or plug 19 is a material that photocrosslinks in response to actinic radiation. This polymeric material is also one that crosslinks into a gel-like consistency so that same will swell and will absorb dyes during formation of the membrane or plug 19. Exemplary base polymers or polymeric backbones in this regard include styrene, styrene derivatives, vinyl pyridine, and the like. Such base polymers or polymeric backbone structures can be modified by attachment of crosslinking functional groups thereto in a manner so as to produce covalently bonded pendant groups. Suitable functional groups for such attachment include vinyl groups, acrylic groups and the like. The thus modified polymers may be further modified by covalent attachment of chemical groups which change one or more properties of the photocrosslinked polymer gels. Such properties include the solubilities of the polymers and the electrical conductivities of the subsequently formed gels. These covalently attached modifiers may introduce chemically reactive sites, introduce chelating or complexing sites, and/or introduce charged sites.

Furthermore, the modified polymers may be crosslinked in the presence of monomers and/or vinyl-containing polymers or acrylic-containing polymers in order thereby to control the swelling properties of the resulting gels. Secondary modifications can also be effected in order to introduce reactive sites, chelating sites, complexing sites, charged sites and the like, and/or to control the electrical conductivity of the resulting gels. If desired, these types of secondary modifications may be effected after the gels have been formed.

The gels are formed in an in situ manner and in place within the distal end portion of the optical fiber. Such formation is initiated and carried out because of the photosensitivity of the polymer material. This is distinguished from typical gel-producing techniques whereby gels are produced by polymerizing monomers that are typically volatile and potentially toxic in the presence of a crosslinker. This type of non-photocrosslinking production requires a time period that is substantially longer than that required when a photocrosslinkable polymer is utilized. Instead, the photocrosslinkable polymers utilized according to the present invention are soluble, high molecular weight polymeric materials that crosslink quickly when suitably initiated by actinic radiation. The polymer solutions adhere to a fiber optic without pretreatment of the fiber optic and by merely dipping the fiber optic into the polymer solution. Compared with conventional crosslinkable polymers, they are relatively easily handled and are capable of being easily and quickly crosslinked in situ, such as at the distal end portion of an optical fiber.

The photocrosslinkability of the polymer can be enhanced by the utilization of a photoinitiator. Typical photoinitiators or photoaccelerators enhance the ability of the photopolymer to absorb actinic energy and to photoreact or photocrosslink. Examples of photoinitiators are acyloins and their derivatives, such as benzion alkyl ethers, α-methylolbenzoin and its ethers and α-methylbenzoin, vicinal diketones and their derivatives, for example diacetyl, benzil, benzil ketals such as benzil ketal, benzil methyl ethyl ketal, benzil methyl benzyl ketal, benzil methyl allyl ketal and benzil ethylene glycol monoketal. Other include unsubstituted and substituted quinones such as anthraquinone and benzanthraquinone, benzophenone and 4,4'-bis-(dimethylamino)-benzophenone and acylphosphine oxide compounds. Additional types of photoinitiators are acridine derivatives, phenazine derivatives, quinoxaline derivatives and quinazoline derivatives.

The photopolymerization initiators can be used individually or as mixtures with one another. The amounts used are those required to initiate the photopolymerization. The photopolymerization initiators could also be used in conjunction with other co-initiators and activators. For example, initiator systems comprising benzoin methyl ether and triphenylphosphine, or comprising 4,4'-bis-(dimethylamino)-benzophenone and a halohydrocarbon or comprising acylphosphine oxide compounds and tertiary amines such as methyldiethanolamine, dimethylethanolamine or triethanolamine may be suitable. Photochromic additives may also be suitable for controlling exposure characteristics.

As used herein, the term actinic radiation means any radiation that will initiate the photopolymerization of the photocrosslinkable material which contains photoreactive moieties that are responsive to the actinic radiation, either alone or in conjunction with a suitable photoinitiator as discussed herein. Included can be laser radiation, short-wave, visible light, long-wave ultraviolet radiation, electron radiation, x-ray radiation and the like.

After the photopolymer material is photocrosslinked into a gel, the resulting gel has a suitable dye absorbed thereinto. This dye will be responsive to the parameter being monitored. The dye acts in the nature of a chemical sensor composition which changes in its optical properties when in the presence of the fluid exhibiting the parameter or parameters being monitored. Typical parameters include pH, oxygen concentration, carbon dioxide concentration, the presence of and concentration of metal ions, the detection of biological fluids, glucose, ammonia, halides and the like, typically within a medical, biological or industrial environment. Dyes possessing these properties are generally known and are sensitive to one or more of these parameters.

Certain dyes exhibit electrical charge properties, and preferably such dyes are used in conjunction with the photocrosslinkable polymer gel membrane or plug that exhibits an opposite electrical charge. Typically, such photocrosslinked polymerizable gel membranes or plugs can exhibit a positive charge, and they would be used in conjunction with dyes exhibiting a negative charge. Whatever dye is used, its absorbtion into the gel membrane or plug should occur after photocrosslinking of the polymeric material into the gel. Otherwise, the actinic radiation would detrimentally alter, for example bleach out, the dye.

Exemplary dyes include absorbence dyes and fluorescent dyes. Typical absorbence dyes include those sensitive to pH and other parameters, exemplary colormetric indicator dyes in this regard including phenol red isothiocyanate, carboxyl phenol red, thymol blue isothiocyanate, bromothymol blue and brilliant yellow. A fluorescent dye such as fluorescein isothiocyanate may be used to reflect pH changes. The signal from a quenchable fluorescent dye such as 9,10-diphenyl anthracene is quenched or diminished by oxygen. Fluorescent dyes typically fall within the general categories of fluoresceins, rhodamines, flavins, coumarins, naphthalenes, acridines, anthrascenes, polynuclear fused hydrocarbons, stilbenes, anthranilinic acids, aminostyrlpyridines, quinolines, salicylic acids, cyanines, oxonols, phenanthidines, fluoroescamines, and derivatives and salts thereof. More specific examples include tetramethyl rhodamine isothiocyanate, eosin isothiocyanate, complexes of transition metals, and the like. Other quenchable fluorescent dyes include rubrene, prylene and decacylene. The dye will be selected in order to provide a gel membrane or plug that is sensitive to the desired parameter.

The resulting photopolymerized gel plug or membrane is a gel that swells to many times its dry volume. The polymeric material itself has the ability to absorb and retain dyes from solutions. In this manner, the photocrosslinkable polymeric material produces polymer gel membranes or matrices on optical fibers. The polymeric material can expand to thousands of times its deswelled volume, and same provides an excellent diffusion barrier or membrane type of structure.

EXAMPLE 1

A copolymer (nominally at a mol ratio of 1 to 9) of p-aminostyrene and 4-vinylpyridine was sequentially treated in dimethylformamide with isocyanatoethyl methacrylate and methyliodide to produce a photocrosslinkable polymeric material. A photoinitiator, typically in an aqueous solution, was combined with the photocrosslinkable polymer. A distal end portion of an optical fiber was immersed therewithin. Thereafter, the polymeric material was photocrosslinked through the use of an arc lamp providing focused ultraviolet light in order to thereby photocure the polymeric material to a gel. The gel is formed through a photocrosslinking chemical reaction. After rinsing, a water insoluble photocrosslinked polymer was provided. This resulting hydrogel had positive charges and acted as an ion exchanger to absorb and retain an anionic dye from an aqueous solution thereof. The hydrogel was capable of proceeding through a number of swelling and deswelling cycles in which the gel expands to thousands of times its deswelled volume. The resulting gel was also surface active and had good adhesive properties.

EXAMPLE 2

Another copolymer having a nominal 1 to 9 mol ratio was prepared, this one being a copolymer of p-aminostyrene and styrene. This copolymer was treated in tetrahydrofuran with isocyanatoethyl methacrylate in order to produce a polymer. This polymer was subsequently photocrosslinked in a tetrahydrofuran solution containing a photoinitiator. The resulting gel plug absorbed and retained neutral dye from a tetrahydrofuran solution.

It will be understood that the embodiments of the present invention which have been described are illustrative of some of the applications of the principles of the present invention. Numerous modifications may be made by those skilled in the art without departing from the true spirit and scope of the invention.

I claim:

1. A method for making a fiber optic chemical sensor for monitoring at least one parameter of a fluid, comprising:
   preparing a photocrosslinkable gel-forming polymer composition including a photopolymer component that crosslinks when subjected to actinic radiation and a solvent within which said photopolymer component is soluble;
   contacting said photocrosslinkable polymer composition with a portion of an optical fiber waveguide in order that the photocrosslinkable polymer composition adheres to the optical fiber waveguide;

subjecting said photocrosslinkable polymer composition to actinic radiation while said composition is adhered to the portion of the optical fiber waveguide to thereby photocrosslink said composition into a photocrosslinked polymeric gel member of said optical fiber; and absorbing a dye component into said photocrosslinked polymeric gel member, said dye component being responsive to a parameter of a fluid to be monitored.

2. The method according to claim 1, wherein said photopolymer component of the photocrosslinkable polymer composition is a vinyl-type base polymer component.

3. The method according to claim 2, wherein said base polymer component is of the vinyl aromatic type.

4. The method according to claim 2, wherein said base polymer component is modified by covalent attachment of moieties selected from the group consisting of vinyl groups, acrylic groups, and combinations thereof.

5. The method according to claim 1, wherein said photocrosslinked polymeric gel member is expandable in volume.

6. The method according to claim 1, wherein said photocrosslinkable composition includes vinyl-containing or acrylic-containing monomers or polymers, and said photocrosslinked polymeric gel member is swellable to at least about one thousand times its dry volume.

7. The method according to claim 1, wherein said photocrosslinkable composition includes a photoinitiator.

8. The method according to claim 1, wherein the photocrosslinked polymeric gel member has electrically charged moieites and wherein said dye component is oppositely charged.

9. The method according to claim 1, wherein said photocrosslinkable polymer is photocrosslinked in the presence of vinyl-containing or acrylic-containing monomers or polymers having reactive sites in order to control swelling of the resulting gels.

10. The method according to claim 1, further including modifying the photocrosslinked polymeric gel member to accomplish secondary modifications selected from the group consisting of introducing reactive sites, chelating sites, complexing sites, and charged sites.

* * * * *

UNITED STATES PATENT AND TRADEMARK OFFICE
CERTIFICATE OF CORRECTION

PATENT NO. : 4,842,783

DATED : June 27, 1989

INVENTOR(S) : Mark E. Blaylock

It is certified that error appears in the above-identified patent and that said Letters Patent is hereby corrected as shown below:

Col. 3, line 52, "used" should read --use--.
Col. 4, line 67, "Other" should read --Others--.

Signed and Sealed this

Thirtieth Day of July, 1991

Attest:

HARRY F. MANBECK, JR.

Attesting Officer

Commissioner of Patents and Trademarks